US012774279B2

(12) United States Patent
Zhang et al.

(10) Patent No.: US 12,774,279 B2
(45) Date of Patent: Oct. 27, 2026

(54) PHTHALIMIDO CEREBLON COMPLEX BINDERS AND TRANSCRIPTION FACTOR DEGRADERS AND METHODS OF USE

(71) Applicant: DANA-FARBER CANCER INSTITUTE, INC., Boston, MA (US)

(72) Inventors: Tinghu Zhang, Brookline, MA (US); Lyn Howard Jones, Winchester, MA (US); Hu Liu, Newton, MA (US); Jianwei Che, Sharon, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 379 days.

(21) Appl. No.: 18/287,347

(22) PCT Filed: Apr. 28, 2022

(86) PCT No.: PCT/US2022/026729

§ 371 (c)(1),
(2) Date: Oct. 18, 2023

(87) PCT Pub. No.: WO2022/232391

PCT Pub. Date: Nov. 3, 2022

(65) Prior Publication Data

US 2024/0217970 A1 Jul. 4, 2024

Related U.S. Application Data

(60) Provisional application No. 63/181,559, filed on Apr. 29, 2021.

(51) Int. Cl.

| | |
|---|---|
| ***C07D 471/04*** | (2006.01) |
| ***A61K 31/437*** | (2006.01) |
| ***A61K 31/444*** | (2006.01) |
| ***C07D 401/14*** | (2006.01) |
| ***C07D 405/14*** | (2006.01) |

(52) U.S. Cl.

CPC .......... *C07D 471/04* (2013.01); *A61K 31/437* (2013.01); *A61K 31/444* (2013.01); *C07D 401/14* (2013.01); *C07D 405/14* (2013.01)

(58) Field of Classification Search

CPC .. C07D 471/04; C07D 401/14; C07D 405/14; A61K 31/437; A61K 31/444

See application file for complete search history.

(56) References Cited

U.S. PATENT DOCUMENTS

| | | | |
|---|---|---|---|
| 8,716,315 | B2 | 5/2014 | Figg et al. |
| 10,647,701 | B2 | 5/2020 | Beckwith et al. |
| 2010/0204227 | A1 | 8/2010 | Muller et al. |
| 2012/0142734 | A1 | 6/2012 | D'Amato |
| 2014/0228333 | A1 | 8/2014 | Adams et al. |
| 2018/0099940 | A1 | 4/2018 | Crew et al. |
| 2018/0215731 | A1 | 8/2018 | Crew et al. |
| 2019/0062309 | A1 | 2/2019 | Beckwith et al. |

FOREIGN PATENT DOCUMENTS

| | | | |
|---|---|---|---|
| WO | 2017197051 | A1 | 11/2017 |
| WO | 2019038717 | A1 | 2/2019 |
| WO | 2019043214 | A1 | 3/2019 |
| WO | 2019060742 | A1 | 3/2019 |
| WO | 2019079569 | A1 | 4/2019 |
| WO | 2019140387 | A1 | 7/2019 |
| WO | 2020012337 | A1 | 1/2020 |
| WO | 2020117759 | A1 | 6/2020 |
| WO | 2020160192 | A1 | 8/2020 |
| WO | 2020160196 | A1 | 8/2020 |
| WO | 2020165833 | A1 | 8/2020 |
| WO | 2020165834 | A1 | 8/2020 |

OTHER PUBLICATIONS

CAS No. 1333622-73-3.
CAS No. 1489856-35-0.
El-Zanfally, S., et al., "Derivatives of Glutarimide Likely to Possess Therapeutic Activity," Journal of Pharmaceutical Sciences, 1965, vol. 54, No. 3, pp. 467-469.
PubChem CID 134482, create date: Aug. 8, 2008 (Aug. 8, 2008) p. 2 formula.
PubChem CID 154680690, create date: Sep. 28, 2020 (Sep. 28, 020) p. 2 formula.
PubChem-SID-383113476, modify date: Apr. 26, 2019, p. 2 figure.

*Primary Examiner* — Alicia L Otton
(74) *Attorney, Agent, or Firm* — ArentFox Schiff LLP; Daniel W. Clarke; Shawn P. Foley

(57) ABSTRACT

Disclosed are compounds and pharmaceutically acceptable salts and stereoisomers thereof that may bind to CRBN complex and cause degradation of various proteins e.g., IKZF2 (Helios). Also disclosed are pharmaceutical compositions containing same, and methods of making and using the compounds to treat diseases and disorders characterized or mediated by the presence of a protein, and hence would benefit from degradation of said protein.

20 Claims, No Drawings

PHTHALIMIDO CEREBLON COMPLEX BINDERS AND TRANSCRIPTION FACTOR DEGRADERS AND METHODS OF USE

RELATED APPLICATIONS

This application is a national stage application, filed under 35 U.S.C. § 371, of International Application No. PCT/US2022/026729, filed Apr. 28, 2022, which claims the benefit of priority under 35 U.S.C. § 119(e) to U.S. Provisional Application No. 63/181,559, filed Apr. 29, 2021, which is incorporated herein by reference in its entirety.

BACKGROUND OF THE INVENTION

Imide molecules, such as thalidomide and its analogs, bind to cereblon (CRBN), a substrate adaptor for the ubiquitously expressed cullin ring ligase 4 (CUL4)-RBXI-DDB1-CRBN (CUL4CRBN) E3 ligase (Kronke et al., Science 343:301-305 (2014); Ito et al., Science 327:1345-1350 (2010)). This results in the recruitment, ubiquitination, and the subsequent proteasomal degradation of neo-substrates, namely Ikaros (IKZF1) and Aiolos (IKZF3), but not any other members of the IKZF zinc finger transcription factor family. CC-885, an imide analog, is predicted to have some activity in inducing Helios degradation, but also induces degradation of GSPT1, a key translation termination factor (Matyskiela et al., Nature 535:252-257 (2016)).

Helios (IKZF2), a member of the IKZF family, is a critical regulator of T cell activity and function. Genetic deletion of Helios resulted in an enhanced anti-tumor immune response (Kim et al., Science 350:334-339 (2015)). Notably, Helios is highly expressed in regulatory T cells (Elkord et al., Expert Opin. Biol. Ther. 12:1423-1425 (2012)), a subpopulation of T cells that restricts the activity of effector T cells. Selective deletion of Helios in regulatory T cells resulted in both loss of suppressive activity and acquisition of effector T cell functions (Najagawa et al., Proc. Natl. Acad. Sci. USA 113:6248-6253 (2016); Yates et al., Proc. Natl. Acad. Sci. USA 115:2162-2167 (2018)). Thus, Helios is a critical factor in restricting T cell effector function in Tregs.

Helios expression has also been reported to be upregulated in 'exhausted' T cells, in the settings of both chronic viral infections (Crawford et al., Immunity 40:289-302 (2014), Doering et al., Immunity 371130-1144 (2012); Scott-Browne el al., Immunity 45:1327-1340 (2016)) and tumors (Martinez et al., Immunity 42:265-278 (2015); Mognol et al., Proc. Natl. Acad. Sci. USA 114:E2776-E2785 (2017); Pereira et al., J. Leukoc. Biol. 102:601-615 (2017); Singer et al., Cell 166:1500-1511 (2016); Schietinger et al., Immunity 45:389-401 (2016)), as well as in dysfunctional chimeric antigen receptor (CAR) T cells (Long et al., Nat. Med. 21:581-590 (2015)). Overexpression or aberrant expression of Helios and various splice isoforms have been reported in several hematological malignancies, including T cell leukemias and lymphomas (Nakase et al., Exp. Hematol. 30:313-317 (2002); Tabayashi et al., Cancer Sci. 98:182-188 (2007); Asanuma et al., Cancer Sci. 104:1097-1106 (2013)). Moreover, knockdown of Helios in a model of mixed lineage leukemia (MLL)-driven myeloid leukemia potently suppressed proliferation and increased cell death (Park et al., J. Clin. Invest. 125:1286-1298 (2015); Park et al., Cell Stem Cell 24:153-165 (2019)).

SUMMARY OF THE INVENTION

A first aspect of the present invention is directed to new compounds which are:

(1)

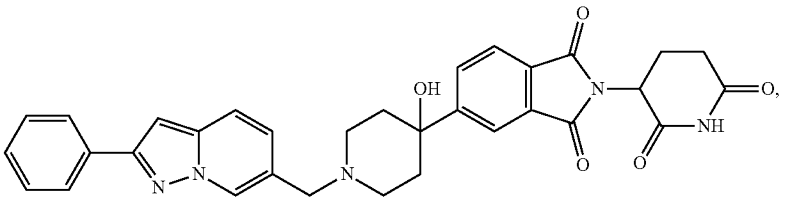

(2)

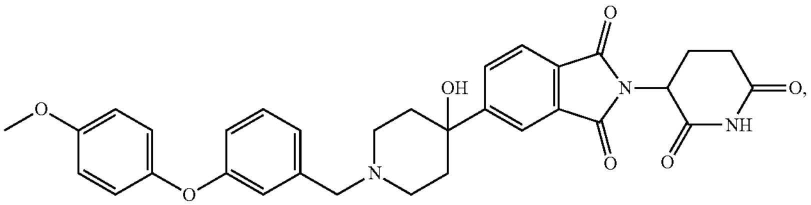

(3)

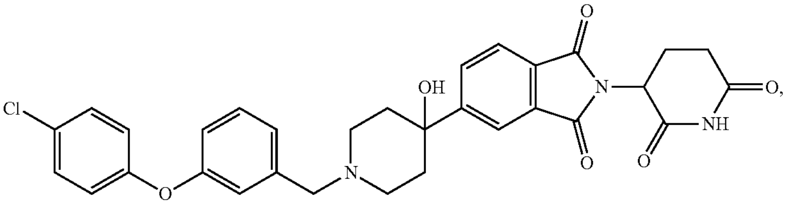

-continued
(4)
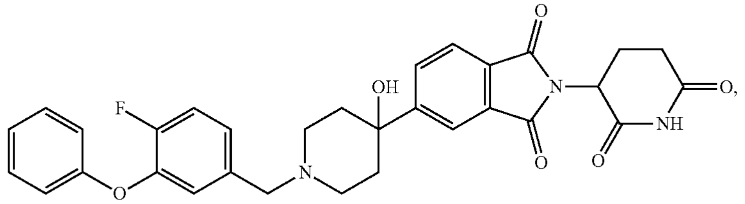
(5)
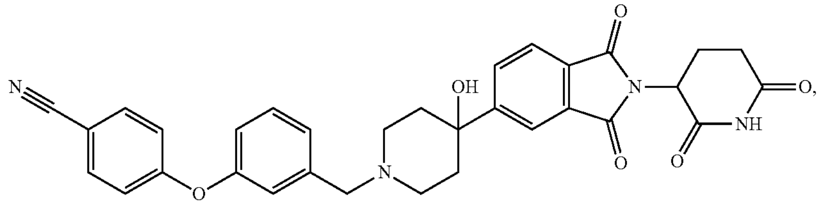
(6)
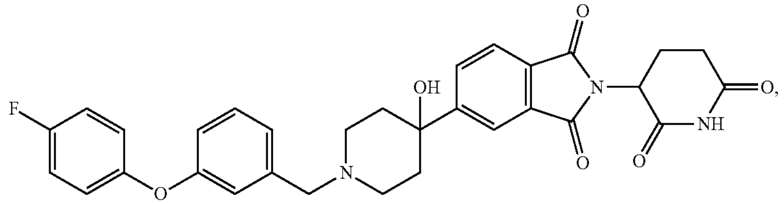
(7)
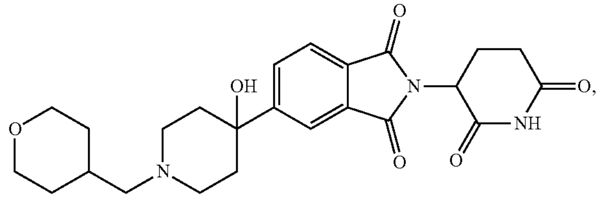
(8)
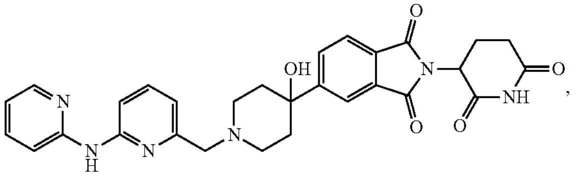
(9)
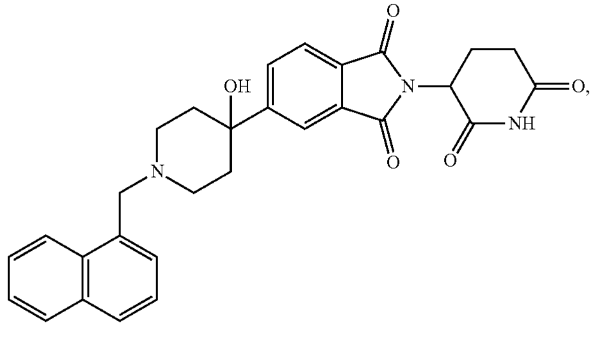
(10)
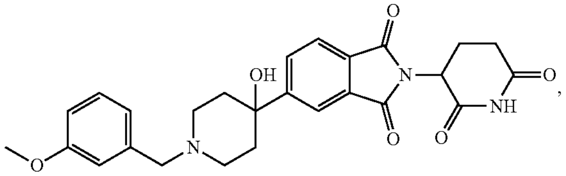
(11)
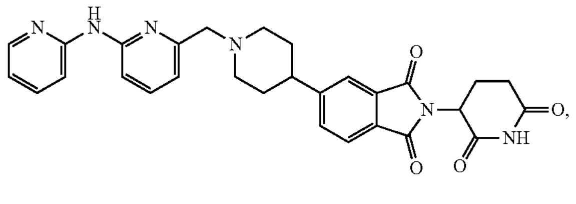
(12)
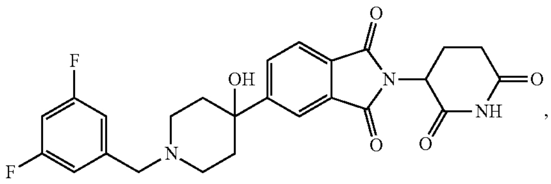

-continued (13)

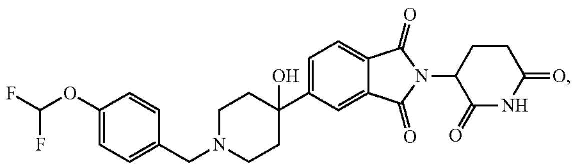

(14)

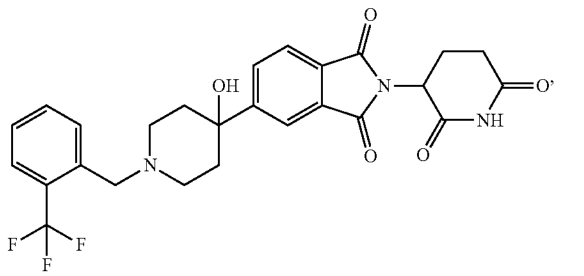

(15)

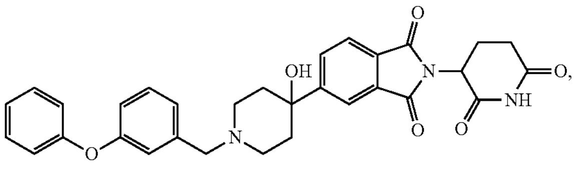

(16)

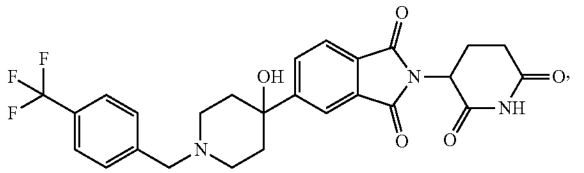

(17)

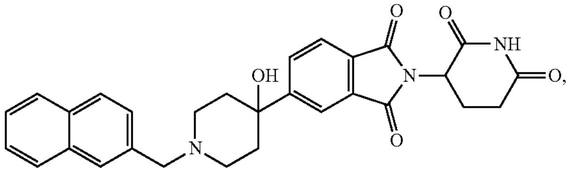

(18)

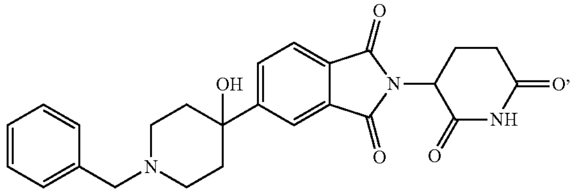

(19)

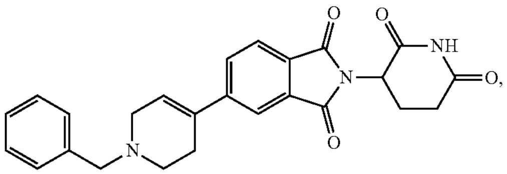

and (20)

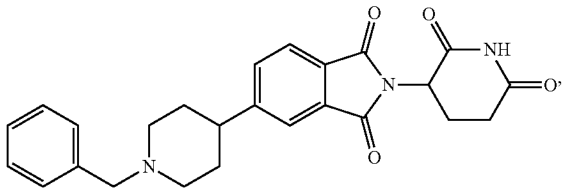

and their pharmaceutically acceptable salts, hydrates, solvates, cocrystals, prodrugs, stereoisomers, and tautomers.

Another aspect of the present invention is directed to a pharmaceutical composition that includes a therapeutically effective amount of any of compounds 1-20 or a pharmaceutically acceptable salt or stereoisomer thereof, and a pharmaceutically acceptable carrier.

Another aspect of the present invention is directed to methods of treating diseases or disorders characterized or mediated by activity of a protein that is a substrate for a complex between cereblon (CRBN) and an inventive compound, that entails the administration of a therapeutically effective amount of any of compounds 1-20 or a pharmaceutically acceptable salt or a stereoisomer thereof, to a subject in need thereof.

In some embodiments, the methods treat diseases or disorders characterized or mediated by Helios activity.

In some embodiments, the disease or disorder is cancer. In some embodiments, the cancer is T cell leukemia, T cell lymphoma, Hodgkin's lymphoma, non-Hodgkin's lymphoma, myeloid leukemia, non-small cell lung cancer (NSCLC), melanoma, triple-negative breast cancer (TNBC), nasopharyngeal cancer (NPC), microsatellite stable colorectal cancer (mssCRC), thymoma, or carcinoid.

As demonstrated in the working examples, compounds of the present invention exhibit degradation of IKZF2 (Helios).

Although not intending to be bound by any particular theory of operation, it is believed that inventive compounds may enhance an anti-tumor immune response by converting regulatory T cells into effector T cells, and by rescuing effector T cell function in exhausted T cells or CAR-T cells.

DETAILED DESCRIPTION OF THE INVENTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2%, or 1%) of the particular value modified by the term "about."

The transitional term "comprising," which is synonymous with "including," "containing," or "characterized by," is inclusive or open-ended and does not exclude additional, unrecited elements, or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In one aspect, compounds of the invention include:

(1)

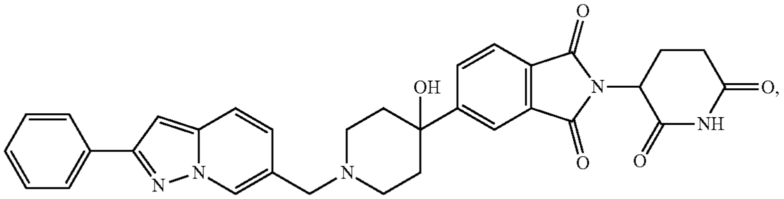

(2)

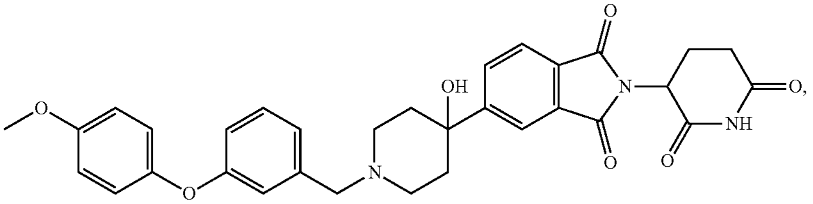

(3)

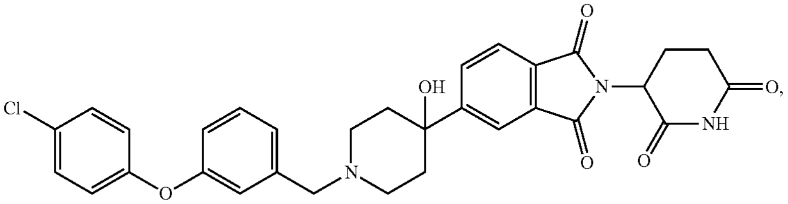

(4)

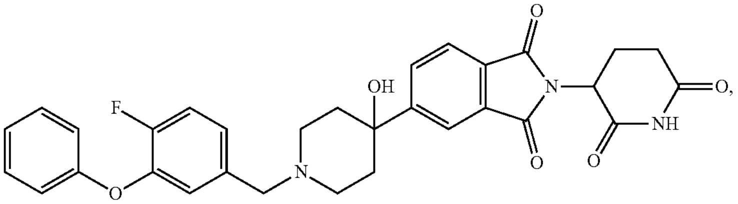

(5)

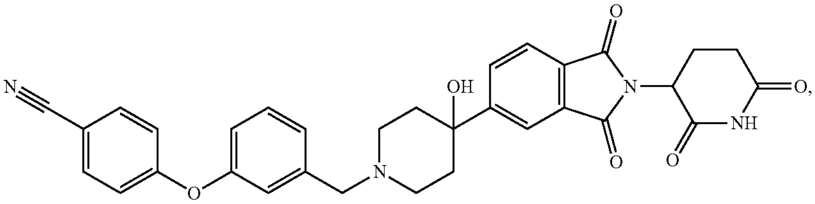

(6)

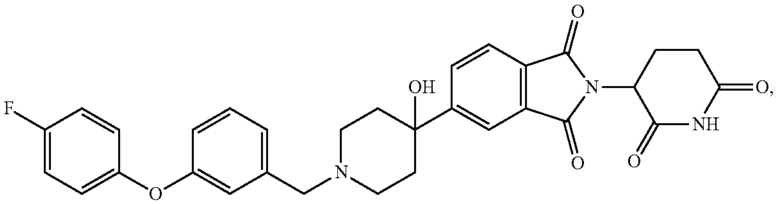

-continued
(7)
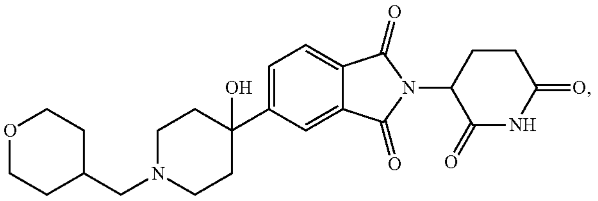
(8)
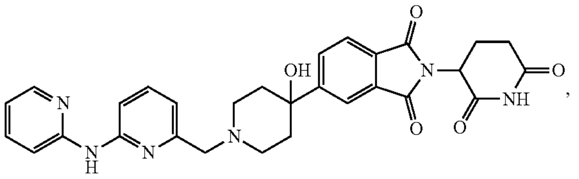
(9)
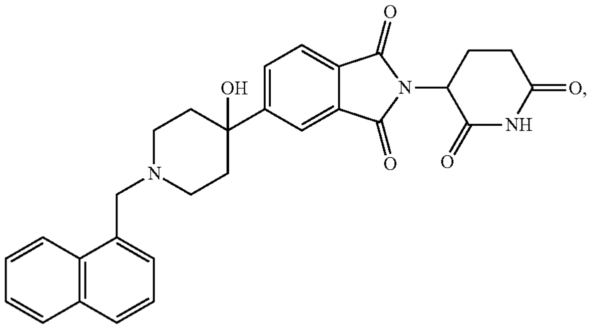
(10)
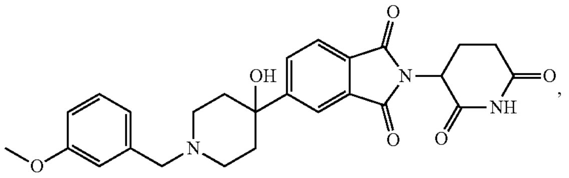
(11)
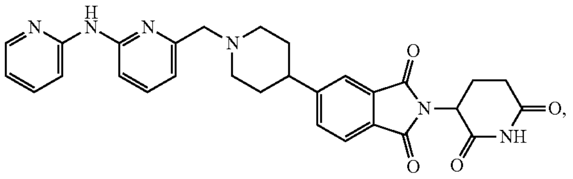
(12)
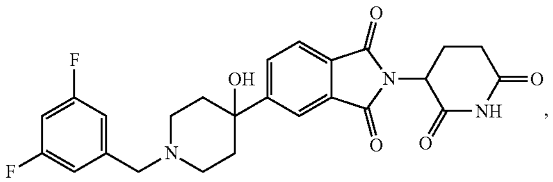
(13)
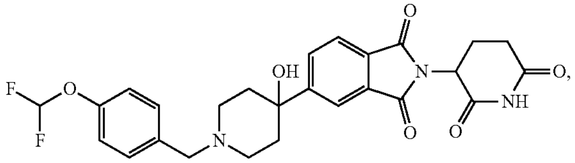
(14)
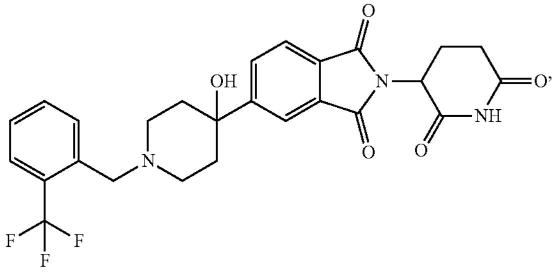
(15)
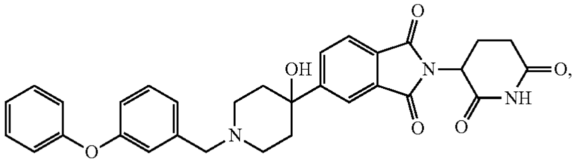
(16)
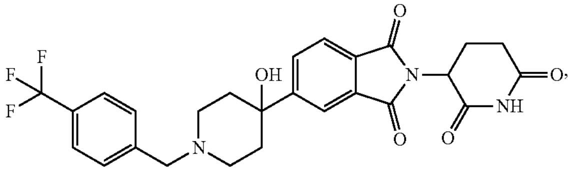
(17)
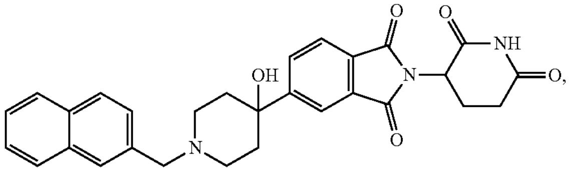
(18)
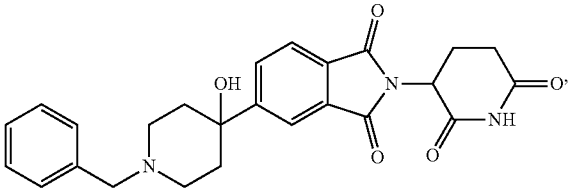

-continued (19)

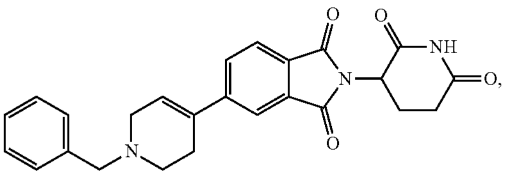

and (20)

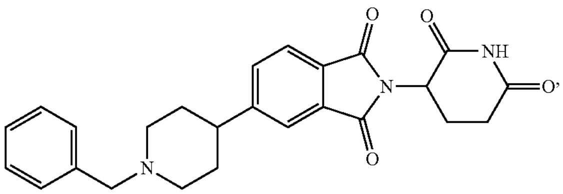

and their pharmaceutically acceptable salts, hydrates, solvates, cocrystals, prodrugs, stereoisomers, and tautomers.

Compounds of the present invention may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin. Suitable base salts include aluminum, calcium, lithium, magnesium, potassium, sodium, or zinc salts.

In some embodiments, the compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

Compounds of the present invention may also be in the form of N-oxides, crystalline forms (also known as polymorphs), active metabolites of the compounds having the same type of activity, prodrugs, tautomers, and unsolvated as well as solvated (e.g., hydrated) forms with pharmaceutically acceptable solvents such as water, ethanol, and the like, of the compounds.

The compounds of the present invention may be prepared by crystallization under different conditions and may exist as one or a combination of polymorphs of the compound. For example, different polymorphs may be identified and/or prepared using different solvents, or different mixtures of solvents for recrystallization, by performing crystallizations at different temperatures, or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other known techniques.

In some embodiments, the pharmaceutical composition comprises a co-crystal of an inventive compound. The term "co-crystal", as used herein, refers to a stoichiometric multi-component system comprising a compound of the invention and a co-crystal former wherein the compound of the invention and the co-crystal former are connected by non-covalent interactions. The term "co-crystal former", as used herein, refers to compounds which can form intermolecular interactions with a compound of the invention and co-crystallize with it. Representative examples of co-crystal formers include benzoic acid, succinic acid, fumaric acid, glutaric acid, trans-cinnamic acid, 2,5-dihydroxybenzoic acid, glycolic acid, trans-2-hexanoic acid, 2-hydroxycaproic acid, lactic acid, sorbic acid, tartaric acid, ferulic acid, suberic acid, picolinic acid, salicyclic acid, maleic acid, saccharin, 4,4'-bipyridine p-aminosalicyclic acid, nicotinamide, urea, isonicotinamide, methyl-4-hydroxybenzoate, adipic acid, terephthalic acid, resorcinol, pyrogallol, phloroglucinol, hydroxyquinol, isoniazid, theophylline, adenine, theobromine, phenacetin, phenazone, etofylline, and phenobarbital.

Methods of Synthesis

In another aspect, the present invention is directed to a method for making an inventive compound, or a pharmaceutically acceptable salt or stereoisomer thereof. Broadly, the inventive compounds may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of an inventive compound or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, compounds of the invention and their pharmaceutically acceptable salts or stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds of the invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The compounds of the invention may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the invention may be formulated for topical administration which as used herein, refers to administration intradermally by invention of the formulation to the epidermis. These types of compositions are typically in the form of ointments, pastes, creams, lotions, gels, solutions and sprays.

Representative examples of carriers useful in formulating compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of an inventive compound or a pharmaceutically acceptable salt or stereoisomer thereof that is effective in producing the desired therapeutic response in a patient suffering from a disease or disorder characterized or mediated by activity of a protein that is a substrate for a complex between cereblon (CRBN). The term "therapeutically effective amount" thus includes the amount of the inventive compound or a pharmaceutically acceptable salt or stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased cells, or reduces the protein that is a substrate for a complex between cereblon (CRBN) in diseased cells. In some embodiments, the disease or disorder is characterized or mediated by IKZF2 (Helios) activity.

The total daily dosage of the compounds and usage thereof may be decided in accordance with standard medical practice, e.g., by the attending physician using sound medical judgment. The specific therapeutically effective dose for any particular subject will depend upon a variety of factors, including the following: the disease or disorder being treated and the severity thereof (e.g., its present status); the activity of the compound employed; the specific composition employed; the age, body weight, general health, sex and diet of the subject; the time of administration, route of administration, and rate of excretion of the compound employed; the duration of the treatment; drugs used in combination or coincidental with the specific compound employed; and like factors well known in the medical arts (see, for example, Hardman et al., eds., *Goodman and Gilman's The Pharmacological Basis of Therapeutics,* 10th Edition, McGraw-Hill Press, 155-173, 2001).

Compounds of the invention may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-10 mg/kg of body weight per day.

Methods of Use

In another aspect, the compounds and pharmaceutically acceptable salts and stereoisomers of the present invention may be useful in the treatment of diseases and disorders characterized or mediated by activity of a protein that is a substrate for a complex between CRBN and an inventive compound, and which participates in the inception, manifestation of one or more symptoms or markers, severity or progression of the disease or disorder, and where the degradation of the targeted protein may confer a therapeutic benefit.

In some embodiments, the present methods are directed to treating diseases or disorders characterized or mediated by IKZF2 (Helios) activity, that entail administration of a therapeutically effective amount of any of compounds 1-20 or a pharmaceutically acceptable salt or stereoisomer thereof, to a subject in need thereof.

A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In some embodiments, compounds 1-20 may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), polycythemia vera, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hepatocellular carcinoma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinemia, melanoma, intraocular (eye) melanoma, Merkle cell carcinoma, mesothelioma, metastatic squamous neck cancer with occult primary, multiple endocrine neoplasia (MEN), myelodysplastic syndromes, essential thrombocythemia, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mixed mesodermal tumor (mixed connective tissue types).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, dysplasia of the liver, hepatocellular carcinoma, intrahepatic cholangiocarcinoma (bile duct cancer), angiosarcoma, hemangiosarcoma, hepatoblastoma, and secondary liver cancer (metastatic liver cancer).

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchoalveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROSI Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, a compound of the present invention may be used to treat T cell leukemia or T cell lymphoma.

In some embodiments, a compound of the present invention may be used to treat Hodgkin's lymphoma or non-Hodgkin's lymphoma.

In some embodiments, a compound of the present invention may be used to treat myeloid leukemia.

In some embodiments, a compound of the present invention may be used to treat non-small cell lung cancer (NSCLC).

In some embodiments, a compound of the present invention may be used to treat melanoma.

In some embodiments, a compound of the present invention may be used to treat triple-negative breast cancer (TNBC).

In some embodiments, a compound of the present invention may be used to treat nasopharyngeal cancer (NPC).

In some embodiments, a compound of the present invention may be used to treat microsatellite stable colorectal cancer (mssCRC).

In some embodiments, a compound of the present invention may be used to treat thymoma.

In some embodiments, a compound of the present invention may be used to treat carcinoid.

In some embodiments, a compound of the present invention may be used to treat gastrointestinal stromal tumor (GIST).

The compounds of the present invention and their pharmaceutically acceptable salts and stereoisomers may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line" as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been unsuccessful, or partially successful but who became non-responsive or intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received prior therapy, such as chemotherapy, radioimmunotherapy, surgical therapy, immunotherapy, radiation therapy, targeted therapy or any combination thereof.

The methods of the present invention may entail administration of an inventive compound or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day off period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

The compounds of the present invention and their pharmaceutically acceptable salts and stereoisomers may be used in combination or concurrently with at least one other active agent e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second agent, the first of the two agents is in some cases still detectable at effective concentrations at the site of treatment. The sequence and time interval may be determined such that they can act together (e.g., synergistically to provide an increased benefit than if they were administered otherwise). For example, the agents may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of the present invention or a pharmaceutically acceptable salt or stereoisomer thereof in combination with one or more additional therapeutic agents known for use in treating the disease or disorder (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional anti-cancer agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immune-modulators, therapeutic antibodies (e.g., mono-specific and bispecific antibodies) and CAR-T therapy. In some embodiments, the combination of a compound of the invention and the additional therapeutic agent is in the form of a co-crystal.

In some embodiments, the compound of the invention and the additional anticancer therapeutic agent may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the compound of the present invention and the additional therapeutic agent (e.g., an anti-cancer therapeutic) are cyclically administered. By way of example in the context of cancer treatment, cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anti-cancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, and depending on the particular cancer being treated, the compound of the present invention may be used in combination with at least one other anti-cancer agents such as Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and non-lymphocytic leukemia), Vincristine (e.g., leukemia), Leucovorin (e.g., colon cancer), Altretamine (e.g., ovarian cancer), Daunorubicin (e.g., acute myeloid leukemia (AML), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymphoma), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastro-intestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer), Temsirolimus (e.g., kidney cancer), Bortezomib (e.g., multiple myeloma and mantle cell lymphoma), Pegaspargase (e.g., acute lymphoblastic leukemia), Cabometyx (e.g., hepatocellular carcinoma, medullary thyroid cancer, and renal cell carcinoma), Pembrolizumab (e.g., cervical cancer, gastric cancer, hepatocellular carcinoma, Hodgkin's lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), Regorafenib (e.g., colorectal cancer, gastrointestinal stromal tumor, and hepatocellular carcinoma), Cemiplimab (e.g., cutaneous squamous cell carcinoma (CSCC)), Avelumab (e.g., Merkel cell carcinoma, urothelial carcinoma, and renal cell carcinoma), Durvalumab (e.g., bladder and lung cancer), Atezolizumab (e.g., urothelial carcinoma, non-small cell lung cancer (NSCLC), triple-negative breast cancer (TNBC), small cell lung cancer (SCLC), and hepatocellular carcinoma (HCC)), and Ipilimumab (e.g., melanoma, non-small cell lung carcinoma (NSCLC), small cell lung cancer (SCLC), bladder cancer, and prostate cancer).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of the present invention or a pharmaceutical composition which contains the compound and a pharmaceutically acceptable carrier wherein the compound and the carrier may be disposed in the same or separate containers. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: Synthesis of 5-(1-benzyl-4-hydroxypiperidin-4-yl)-2-(2,6-dioxopiperidin-3-yl)isoindoline-1,3-dione (18)

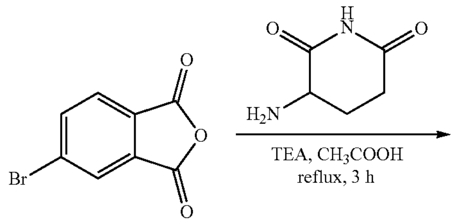

-continued

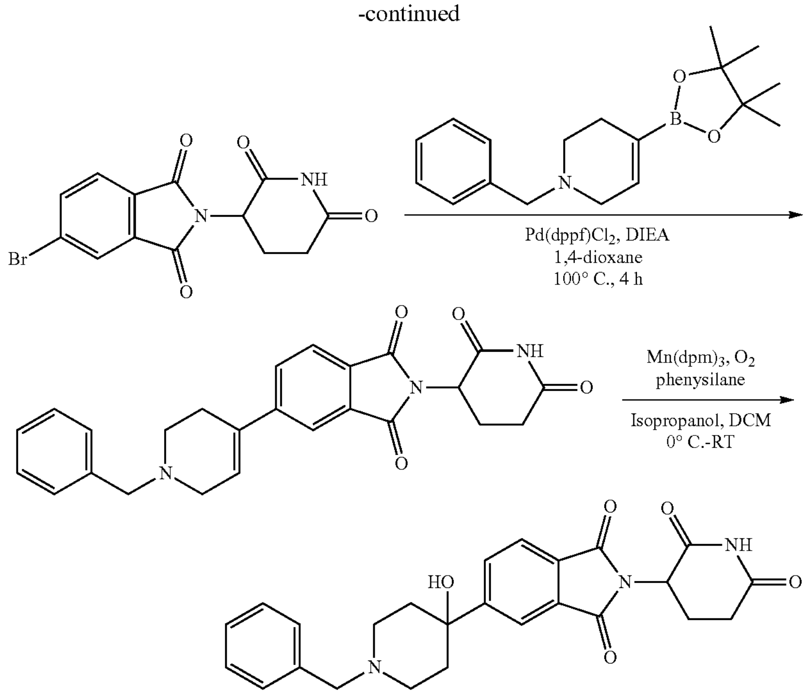

5-Bromo-2-(2,6-dioxopiperidin-3-yl)isoindoline-1,3-dione

A solution of 5-bromoisobenzofuran-1,3-dione (10 g, 44.2 mmol) and 3-aminopiperidine-2,6-dione hydrochloride (7.2 g, 44.2 mmol) in 200 mL of $CH_3COOH$ was heated at 150° C. for 4 hours. The mixture was then cooled to room temperature (rt) and water (100 mL) was added. The suspension stirred for 15 minutes. The suspension was filtered and the title compound was isolated as a grey solid (7 g, 47.1%). MS (M+H+): 336.93.

5-(1-Benzyl-1,2,3,6-tetrahydropyridin-4-yl)-2-(2,6-dioxopiperidin-3-yl)isoindoline-1,3-dione Pd$(t\text{-}Bu_3P)_2$ (1.51 g, 2.96 mmol) and DIEA (3.82 g, 29.6 mmol) was added to a solution of 5-bromo-2-(2,6-dioxopiperidin-3-yl)isoindoline-1,3-dione (5 g, 14.8 mmol), 1-benzyl-4-(4,4,5,5-tetramethyl-1,3,2-dioxaborolan-2-yl)-1,2,3,6-tetrahydropyridine (17.7 g, 59.2 mmol) in 50 mL of 1,4-dioxane. The mixture stirred at 100° C. under protection of nitrogen for 4 hours. The mixture was then filtered and the filtrate was concentrated under reduced pressure. The residue was dissolved in 200 mL of dichloromethane (DCM), and the DCM was removed slowly under reduced pressure, until around 25 mL of DCM remained. A solid formed and was filtered to give the title compound as a grey solid (2 g, 31.7%). MS ($M+H^+$): 430.21.

5-(1-Benzyl-4-hydroxypiperidin-4-yl)-2-(2,6-dioxopiperidin-3-yl)isoindoline-1,3-dione (18)

A solution of 5-(1-benzyl-1,2,3,6-tetrahydropyridin-4-yl)-2-(2,6-dioxopiperidin-3-yl)isoindoline-1,3-dione (80 mg, 0.186 mmol) in 50 mL of isopropanol and 200 mL of DCM was cooled to 0° C. Mn$(dpm)_3$ (56.3 mg, 0.93 mmol) was then added. The mixture stirred at rt for 16 hours under $O_2$ atmosphere. The mixture was then concentrated and purified by prep-HPLC to give the title compound as a white solid (45 mg, 54.2%). $^1H$ NMR (400 MHz, DMSO-$d_6$) δ 11.12 (s, 1H), 8.01-7.98 (m, 2H), 7.86 (d, J=8.3 Hz, 1H), 7.37-7.30 (m, 4H), 7.25 (td, J=6.5, 6.1, 2.8 Hz, 1H), 5.29 (d, J=26.6 Hz, 1H), 5.14 (dd, J=12.9, 5.4 Hz, 1H), 3.54 (s, 2H), 2.89 (ddd, J=18.2, 13.8, 5.4 Hz, 1H), 2.66 (d, J=10.9 Hz, 2H), 2.58-2.54 (m, 1H), 2.46 (s, 1H), 2.03 (qd, J=12.8, 10.5, 3.6 Hz, 3H), 1.61 (d, J=12.8 Hz, 2H). MS (M+H): 448.23.

Example 2: Synthesis of 2-(2,6-dioxo-3-piperidyl)-5-[4-hydroxy-1-(2-naphthylmethyl)-4-piperidyl]isoindoline-1,3-dione (17

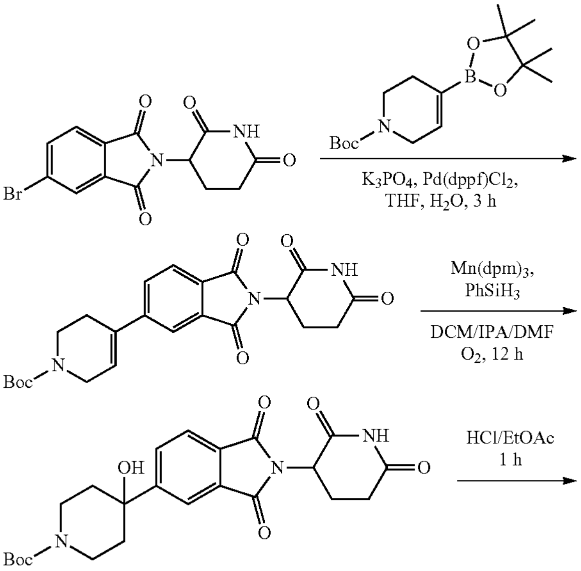

-continued

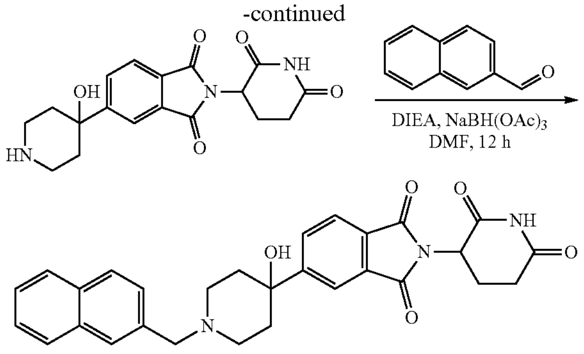

tert-Butyl 4-[2-(2,6-dioxo-3-piperidyl)-1,3-dioxo-isoindolin-S-yl]-3,6-dihydro-2H-pyridine-1-carboxylate Di-tert-butyl(cyclopentyl)phosphane dichloropalladium iron (966 mg, 1.48 mmol) was added to a solution of tert-butyl 4-(4,4,5,5-tetramethyl-1,3,2-dioxaborolan-2-yl)-3,6-dihydro-2H-pyridine-1-carboxylate (6.88 g, 22.25 mmol), 5-bromo-2-(2,6-dioxo-3-piperidyl) isoindoline-1,3-dione (5 g, 14.83 mmol) and $K_3PO_4$ (6.30 g, 29.66 mmol) in THF (50 mL) and $H_2O$ (12 mL) and the mixture stirred at 80° C. for 3 hours. After completion of the reaction, the mixture was concentrated under reduced pressure to give a residue. The residue was diluted with saturated aq. $NaHCO_3$ (800 mL) and extracted with EtOAc (200 mL×2). The combined organic layers were washed with brine (100 mL×2), dried over $Na_2SO_4$ and concentrated under reduced pressure to give a residue. The residue was purified by silica gel chromatography (eluent of 0-100% ethyl acetate/petroleum ether) to afford the title compound as a brown solid (6.5 g, 14.79 mmol). $^1$H NMR (400 MHz, methanol-$d_4$) δ ppm 7.95 (s, 1H), 7.83-7.93 (m, 2H), 6.41 (br s, 1H), 5.16 (dd, J=12.63, 5.50 Hz, 1H), 4.15 (br s, 2H), 3.69 (t, J=5.32 Hz, 2H), 2.84-2.95 (m, 1H), 2.69-2.82 (m, 2H), 2.62 (d, J=1.63 Hz, 2H), 2.16 (dd, J=5.16, 2.25 Hz, 1H), 1.52 (s, 9H).

tert-Butyl 4-[2-(2,6-dioxo-3-piperidyl)-1,3-dioxo-isoindolin-5-yl]-4-hydroxy-piperidine-1-carboxylate tris-[(Z)-1-tert-butyl-4,4-dimethyl-3-oxo-pent-1-enoxy] manganese (1.38 g, 2.28 mmol) and phenylsilane (985 mg, 9.10 mmol) were added to a solution of tert-butyl 4-[2-(2,6-dioxo-3-piperidyl)-1,3-dioxo-isoindolin-5-yl]-3,6-dihydro-2H-pyridine-1-carboxylate (2 g, 4.55 mmol) in DCM (10 mL), isopropanol (10 mL) and DMF (5 mL) at 0° C. The mixture stirred at 20° C. for 12 hours under an oxygen atmosphere. After completion of the reaction, it was concentrated under reduced pressure to give a residue. The residue was purified by silica gel column chromatography (petroleum ether/ethyl acetate=10/1 to 1/1) to afford the title compound as a white solid (0.6 g, 1.18 mmol).

2-(2,6-Dioxo-3-piperidyl)-5-(4-hydroxy-4-piperidyl) isoindoline-1,3-dione

HCl/EtOAc (4 M, 2 mL) was added to a solution of tert-butyl 4-[2-(2,6-dioxo-3-piperidyl)-1,3-dioxo-isoindolin-5-yl]-4-hydroxy-piperidine-1-carboxylate (600 mg, 1.31 mmol) in EtOAc (4 mL) and the mixture stirred at 15° C. for 1 hour. After completion of the reaction, it was concentrated under reduced pressure to afford the title compound as a yellow solid (470 mg, 1.19 mmol, HCl salt). $^1$H NMR (400 MHz, methanol-$d_4$) δ ppm 7.96 (d, J=1.0 Hz, 1H), 7.94-7.90 (m, 1H), 7.84-7.81 (m, 1H), 5.09-5.03 (m, 1H), 3.44-3.26 (m, 4H), 2.80-2.72 (m, 1H), 2.71-2.60 (m, 2H), 2.27-2.15 (m, 2H), 2.05 (dtd, J=2.4, 5.2, 12.6 Hz, 1H), 1.88 (d, J=13.9 Hz, 2H).

2-(2,6-Dioxo-3-piperidyl)-S-[4-hydroxy-J-(2-naphthylmethyl)-4-piperidyl]isoindoline-1,3-dione (17)

DIEA (53 mg, 0.41 mmol) and $NaBH(OAc)_3$ (129 mg, 0.61 mmol) were added to a solution of 2-(2,6-dioxo-3-piperidyl)-5-(4-hydroxy-4-piperidyl)isoindoline-1,3-dione (80 mg, 0.20 mmol, HCl salt) and naphthalene-2-carbaldehyde (64 mg, 0.41 mmol) in DMF (1 mL) and the mixture stirred at 60° C. for 12 hours. After completion of the reaction, it was purified by prep-HPLC to afford the title compound as a white solid (66 mg, 0.13 mmol, 63%). $^1$H NMR (400 MHz, methanol-$d_4$) δ ppm 8.17-8.12 (m, 1H), 8.08-8.03 (m, 2H), 8.03-7.95 (m, 3H), 7.95-7.90 (m, 1H), 7.72-7.66 (m, 1H), 7.66-7.56 (m, 2H), 5.27-5.08 (m, 1H), 4.63 (s, 2H), 3.70-3.51 (m, 4H), 2.95-2.83 (m, 1H), 2.82-2.68 (m, 2H), 2.49-2.31 (m, 2H), 2.21-2.11 (m, 1H), 2.05 (d, J=14.3 Hz, 2H). MS (M+H$^+$): 498.1.

Example 3: Synthesis of 2-(2,6-dioxo-3-piperidyl)-5-[4-hydroxy-1-[(2-phenylpyrazolo[1,5-a]pyridin-6-yl)methyl]-4-piperidyl]isoindoline-1,3-dione (1)

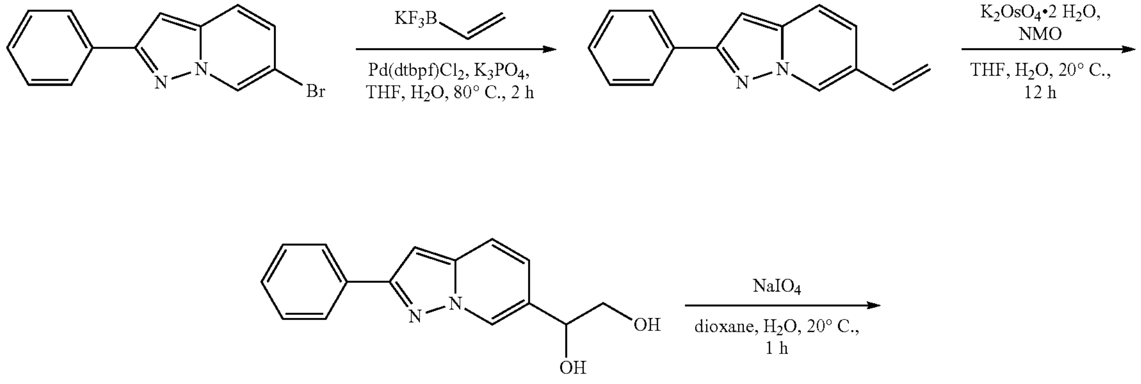

-continued

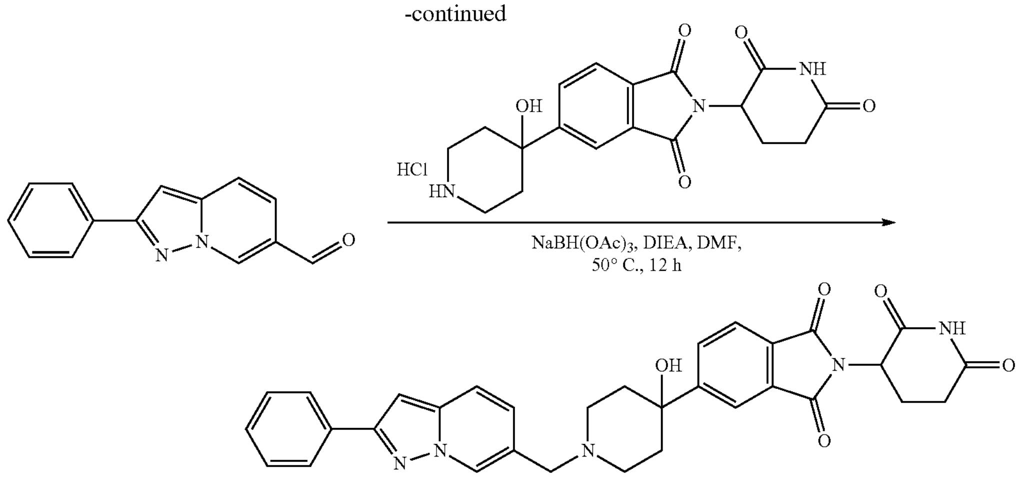

2-Phenyl-6-vinyl-pyrazolo[1,5-a]pyridine

A mixture of 6-bromo-2-phenyl-pyrazolo[1,5-a]pyridine (1.34 g, 4.91 mmol), potassium trifluoro(vinyl)boranuide (986 mg, 7.36 mmol), di-tert-butyl(cyclopentyl)phosphane; dichloropalladium iron (320 mg, 0.49 mmol), and $K_3PO_4$ (2.08 g, 9.81 mmol) in THF (16 mL) and $H_2O$ (4 mL) was degassed and purged with $N_2$ for 3 times, and then the mixture stirred at 80° C. for 2 hours under $N_2$ atmosphere. The reaction mixture was poured into $H_2O$ (100 mL) and extracted with EtOAc (100 mL×3). The combined organic layers were washed with brine (100 mL×2), dried over $Na_2SO_4$, filtered and concentrated under reduced pressure to give a residue, which was purified by silica gel chromatography (petroleum ether/ethyl acetate=1:0 to 20:1) to afford the title compound as a yellow solid (1.2 g, 0.59 mmol, 73%). $^1$H NMR (400 MHz, DMSO-$d_6$) δ ppm 8.78 (s, 1H), 7.98 (d, J=7.4 Hz, 2H), 7.66 (d, =9.3 Hz, 1H), 7.56-7.44 (m, 3H), 7.42-7.35 (m, 1H), 7.06 (s, 1H), 6.77 (dd, J=11.1, 17.6 Hz, 1H), 5.90 (d, J=17.5 Hz, 1H), 5.33 (d, J=11.0 Hz, 1H). MS (M+H$^+$): 221.2.

1-(2-Phenylpyrazolo[1,5-a]pyridin-6-yl)ethane-1,2-diol $K_2OsO_4 \cdot 2H_2O$ (33 mg, 0.091 mmol) and NMO (319 mg, 2.72 mmol) were added to a solution of 2-phenyl-6-vinyl-pyrazolo[1,5-a]pyridine (0.2 g, 0.91 mmol) in THF (2 mL) and $H_2O$ (0.2 mL). The mixture stirred at 20° C. for 12 hours. The reaction mixture was poured into $H_2O$ (10 mL) and extracted with EtOAc (10 mL×3). The combined organic layers were washed with brine (10 mL×2), dried over $Na_2SO_4$, and concentrated under vacuum to yield the title compound as a yellow solid (0.17 g) as a yellow solid. MS (M+H$^+$): 255.2.

2-Phenylpyrazolo[1,5-a]pyridine-6-carbaldehyde $NaIO_4$ (286 mg, 1.34 mmol) was added to a solution of 1-(2-phenylpyrazolo[1,5-a]pyridin-6-yl)ethane-1,2-diol (0.17 g, 0.67 mmol) in dioxane (2 mL) and $H_2O$ (0.2 mL) and the mixture stirred at 20° C. for 1 hour. The reaction mixture was poured into $H_2O$ (10 mL), and extracted with EtOAc (10 mL×3). The combined organic layers were washed with brine (10 mL×2), dried over $Na_2SO_4$, filtered and concentrated under reduced pressure to give a residue which was purified by silica gel chromatography (petroleum ether/ethyl acetate=1:0 to 10:1) to afford the title compound as a white solid (0.1 g, 0.45 mmol, 67%). $^1$H NMR (400 MHz, DMSO-$d_6$) δ ppm 9.94 (s, 1H), 9.50 (s, 1H), 8.04 (d, J=7.9 Hz, 2H), 7.78 (d, J=9.1 Hz, 1H), 7.52 (dd, J=6.8, 7.8 Hz, 3H), 7.46 (d, J=7.4 Hz, 1H), 7.27 (s, 1H). MS (M+H$^+$): 223.1.

2-(2,6-Dioxo-3-piperidyl)-S-[4-hydroxy-1-[(2-phenylpyrazolo[1,5-a]pyridin-6-yl)methyl]-4-piperidyl]isoindoline-1,3-dione (1)

Compound 1 was prepared following a similar procedure as in Example 2. $^1$H NMR (400 MHz, DMSO-$d_6$) δ ppm 11.16-11.01 (m, 2H), 9.02 (s, 1H), 8.01 (d, J=7.4 Hz, 2H), 7.98-7.87 (m, 3H), 7.82-7.74 (m, 1H), 7.55 (d, J=10.1 Hz, 1H), 7.52-7.46 (m, 2H), 7.44-7.38 (m, 1H), 7.15 (s, 1H), 5.96 (s, 1H), 5.15 (dd, J=5.3, 12.9 Hz, 1H), 4.46 (d, J=4.5 Hz, 2H), 3.42-3.28 (m, 4H), 2.95-2.83 (m, 1H), 2.65-2.51 (m, 4H), 2.08-2.01 (m, 1H), 1.86 (d, J=13.5 Hz, 2H). MS (M+H$^+$): 564.0.

Example 4: Liquid Chromatography Mass Spectrometry (LCMS) Data

Reaction monitoring and final compound characterization were done using Shimadzu LC-20AD series (binary pump and diode array detector) with Luna-C18 column (3 μm, 2.0×30 mm). Mobile phase: A: 0.04% Trifluoroacetic acid in water (v/v), B: 0.02% Trifluoroacetic acid in MeCN (v/v). Flow Rate: 1 mL/min (0.00-1.80 min) and 1.2 mL/min (1.81-2.00 min) at 25° C. MS: 2020, Quadrupole LC/MS, Ion Source: API-ESI, TIC: 100~1000 m/z; Drying gas flow: 15 L/min; Nebulizer pressure: 1.5 L/min; Drying gas temperature: 250° C., Vcap: 1400V.

TABLE 1

LCMS data of inventive compounds

| Compound # | Calculated Mass (g/mol) | Observed Mass (M + H) | Compound # | Calculated Mass | Observed Mass (M + H) |
|---|---|---|---|---|---|
| 1 | 563.2 | 564.0 | 11 | 524.2 | 525.1 |
| 2 | 569.2 | 570.1 | 12 | 483.2 | 484.2 |
| 3 | 573.2 | 574.0 | 13 | 513.2 | 514.1 |

TABLE 1-continued

| LCMS data of inventive compounds | | | | | |
|---|---|---|---|---|---|
| Compound # | Calculated Mass (g/mol) | Observed Mass (M + H) | Compound # | Calculated Mass | Observed Mass (M + H) |
| 4 | 557.2 | 558.1 | 14 | 515.2 | 516.1 |
| 5 | 564.2 | 565.1 | 15 | 539.2 | 540.1 |
| 6 | 557.2 | 558.1 | 16 | 515.2 | 516.1 |
| 7 | 455.2 | 456.1 | 17 | 497.2 | 498.1 |
| 8 | 540.2 | 541.1 | 18 | 447.2 | 448.2 |
| 9 | 497.2 | 498.1 | 19 | 429.2 | 430.2 |
| 10 | 477.2 | 478.1 | 20 | 431.2 | 432.3 |

Example 5: Cellular CRBN NanoBret™ Engagement Assay

HEK293T cells were transduced with lentivirus and put under puromycin selection (5 μg/mL) for two weeks to produce a cell line stably expressing CRBN with N-terminally fused NanoLuc luciferase (NanoLuc®-CRBN). After antibiotic selection, cells were cultured in DMEM (Gibco, Life Technologies™) supplemented with 10% FBS and 1 μg/mL puromycin to maintain stable NanoLuc®-CRBN expression.

To run the assay, cells were cultured to confluency in 10 $cm^2$ tissue culture treated plates (Corning®, 430165), washed with PBS and trypsinized at room temperature to detach from the cell culture plate. After 3-4 minutes, the trypsin was quenched with 5× volume DMEM media (Gibco, Life Technologies™) with 10% FBS and cells are collected by centrifugation (1000 rpm, 5 min). The supernatant was removed by vacuum aspiration and the pellet was then resuspended in Opti-MEM™ without phenol red. The density of this cell suspension was determined by diluting the cells 1:1 with trypan blue, then counting using a Countess™ II (Thermo Fischer Scientific) and then diluted to the required volume at $2\times10^5$ viable cells/mL in Opti-MEM™ I (Gibco, Life Technologies™). CRBN engagement tracer (stock at 10 μM in 31.25% PEG-400, 12.5 mM HEPES, pH 7.5, filtered using a 0.22 μm nitrocellulose membrane; final concentration in cell suspension for assay at 250 nM) was added to the suspension. Cells were then plated in a white/opaque cell culture treated 384-well plate (Corning®, 3570) at volume of 50 μL/well. After plating, the assay plate was centrifuged (500×g, 5 min) and covered in aluminum foil. Compounds for testing were added to the plate using D300e Digital Dispenser (HP) in duplicate 12-pt titrations from a 10 mM stock in DMSO, with DMSO normalized to 1% total volume. The plate was then placed in an incubator at 37° C., 5% $CO_2$ for two hours. After incubation, the plate was removed and set on the bench to come to room temperature (~10-15 min). The NanoLuc® substrate (500× solution)* and extracellular inhibitor (1500× solution)* were diluted in Opti-MEM™ I (Gibco, Life Technologies™) to prepare a 3× solution. This was then added to each well (25 μL/well). The plate was read on a Pherastar® FSX microplate reader with simultaneous dual emission capabilities to read 384-well plates at 450 and 520 nm. The NanoBRET™ ratio was calculated by dividing the signal at 520 nm by the signal at 450 nm for each sample. Duplicate points were averaged and plotted against [compound, M] to generate an ECso curve.

The results are shown in Table 2. The data demonstrate that the compounds of the invention bind cereblon in cells.

TABLE 2

| CRBN engagement of inventive compounds | |
|---|---|
| Compound # | $IC_{50}$ (M) |
| 1 | $3.8 \times 10^{-8}$ |
| 2 | $4.1 \times 10^{-8}$ |
| 3 | $5.4 \times 10^{-8}$ |
| 4 | $8.8 \times 10^{-8}$ |
| 5 | $2.4 \times 10^{-8}$ |
| 6 | $<2.6 \times 10^{-9}$ |
| 7 | $5.6 \times 10^{-8}$ |
| 8 | $7.6 \times 10^{-8}$ |
| 9 | $1.5 \times 10^{-8}$ |
| 11 | $2.4 \times 10^{-7}$ |
| 14 | $6.2 \times 10^{-8}$ |
| 15 | $3.1 \times 10^{-8}$ |
| 17 | $2.0 \times 10^{-7}$ |
| 18 | $6.5 \times 10^{-8}$ |
| 19 | $1.7 \times 10^{-6}$ |

Example 6: HiBiT PROTOCOL

The HiBiT protein tagging system was applied to MOLT4 cells via a CRISPR/Cas-mediated insertion of the HiBiT peptide tag (Promega™) to the N-terminus of the IKZF2 gene locus (Neon™ Transfection System). The resulting HiBiT-Helios stable cell line was treated with inventive compounds 1-10 in triplicates following a 13-point concentration scheme ranging from 10 μM to 0.00026 μM. At the indicated timepoints, the Nano-Glo® HiBiT Lytic Detection system (Promega™) was utilized for detecting bioluminescence of the HiBiT tag in treated cells: the abundance of the tag is proportionate to the level of luminescence. Following normalization to DMSO, dose-response curves were plotted (GraphPad Prism) to determine the concentration points at which 50% of HiBiT-Helios degradation was achieved by each compound. The extent of degradation (range of luminescence) from the highest to lowest concentration points was calculated to determine Dmax.

The results are shown in Table 3. The data demonstrate that the compounds of the invention degrade IKZF2 (Helios) as measured using the HiBit-IKZF2 assay.

TABLE 3

| Degradation Activity (HiBiT-IKZF2 assay) of inventive compounds | | |
|---|---|---|
| Compound # | Cellular Degradation - IKZF2 $DC_{50}$ (M) | % IKZF2 Degradation at 10 μM |
| 1 | $4.9 \times 10^{-9}$ | 80 |
| 2 | $5.1 \times 10^{-9}$ | 80 |
| 3 | $8.8 \times 10^{-9}$ | 79 |
| 4 | $2.3 \times 10^{-8}$ | 73 |
| 5 | $4.3 \times 10^{-9}$ | 77 |
| 6 | $7.3 \times 10^{-9}$ | 77 |
| 7 | $5.5 \times 10^{-8}$ | 55 |
| 8 | $2.4 \times 10^{-8}$ | 71 |
| 9 | $1.4 \times 10^{-8}$ | 72 |
| 10 | $1.6 \times 10^{-8}$ | 77 |
| 11 | — | 45 |
| 12 | $6.1 \times 10^{-8}$ | 76 |
| 13 | $1.9 \times 10^{-8}$ | 74 |
| 14 | $2.0 \times 10^{-8}$ | 57 |
| 15 | $4.2 \times 10^{-9}$ | 76 |
| 16 | $5.6 \times 10^{-8}$ | 69 |
| 17 | $1.3 \times 10^{-8}$ | 80 |
| 18 | $2.2 \times 10^{-8}$ | 70 |
| 19 | — | 30 |
| 20 | — | 45 |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound which is:

(1)

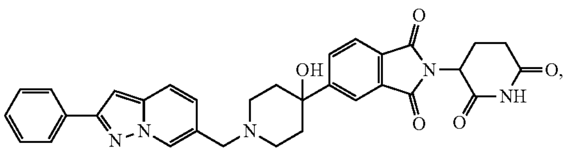

(2)

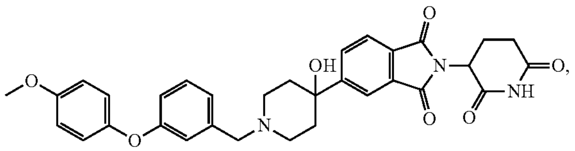

(3)

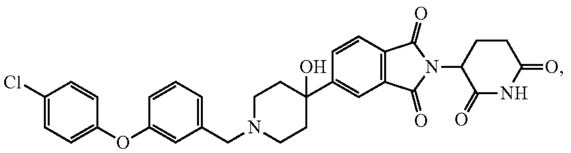

(4)

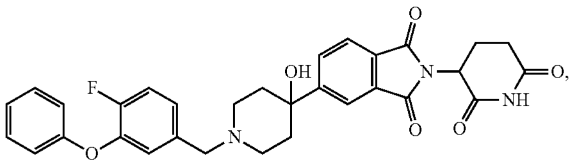

(5)

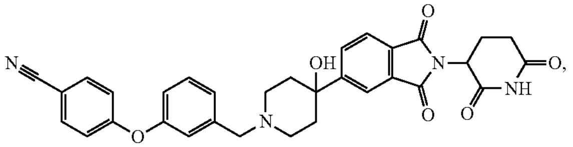

(6)

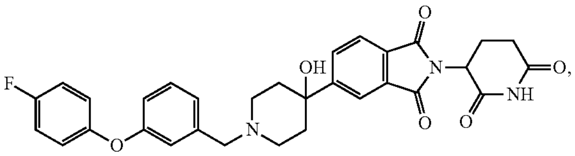

(7)

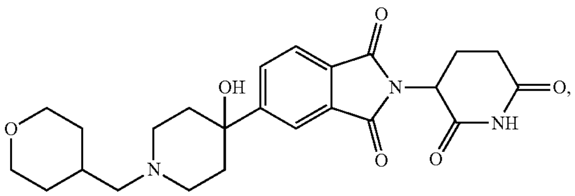

-continued
(8)
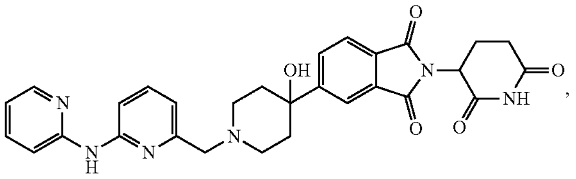
(9)
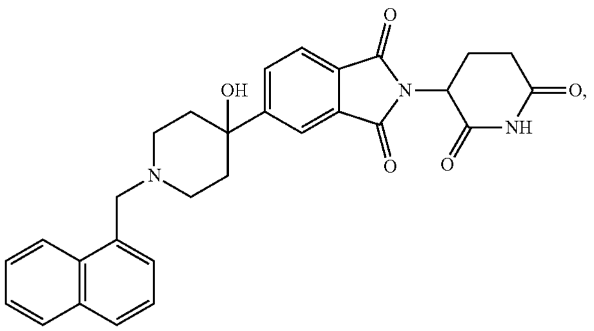
(10)
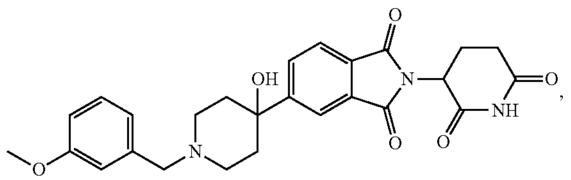
(11)
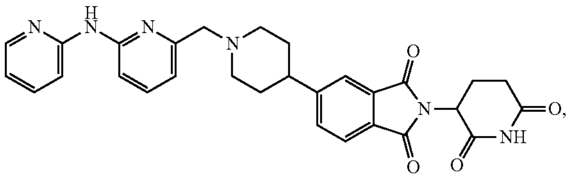
(12)
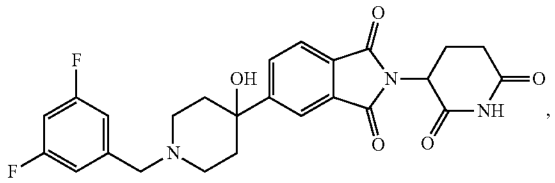
(13)
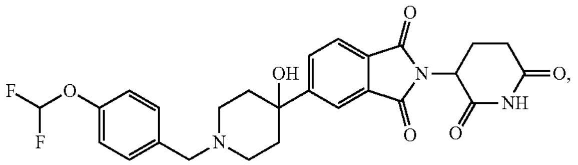
(14)
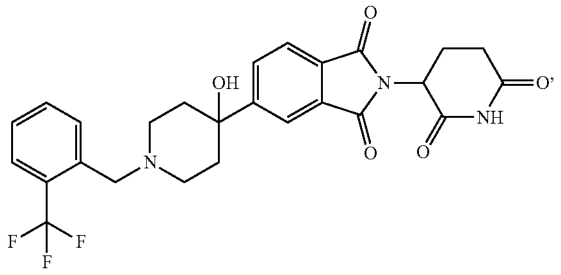
(15)
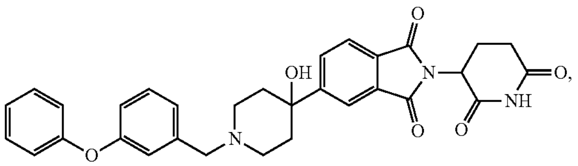
(16)
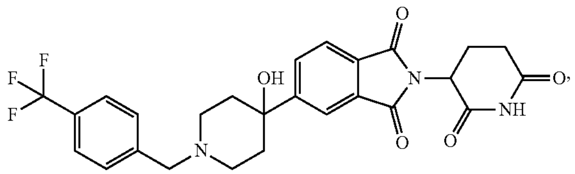
(17)
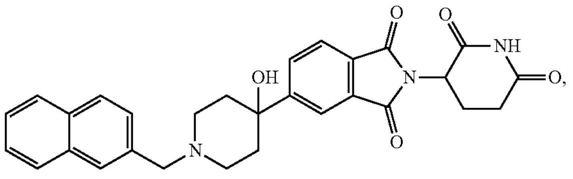
(18)
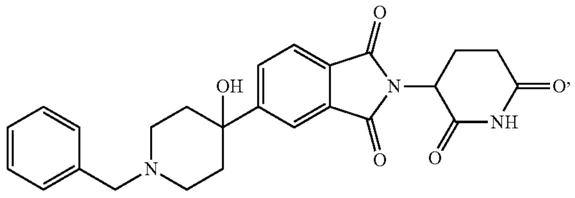

-continued (19)

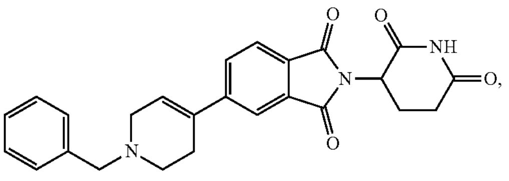

or (20)

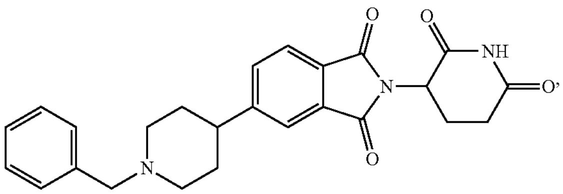

or a pharmaceutically acceptable salt, hydrate, solvate, cocrystal, prodrug, stereoisomer, or tautomer thereof.

2. The compound of claim 1, which is (1)

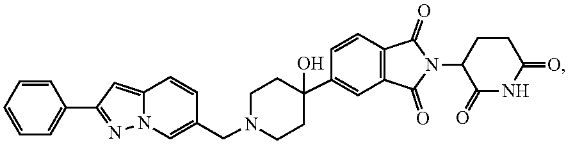

or a pharmaceutically acceptable salt thereof.

3. The compound of claim 1, which is (2)

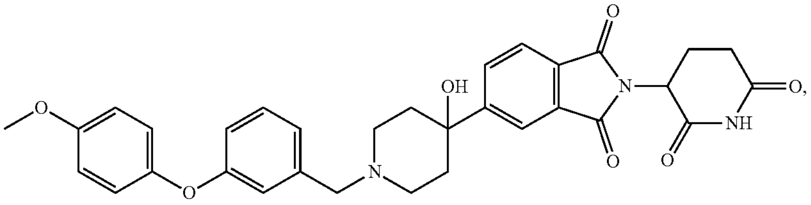

or a pharmaceutically acceptable salt thereof.

4. The compound of claim 1, which is (3)

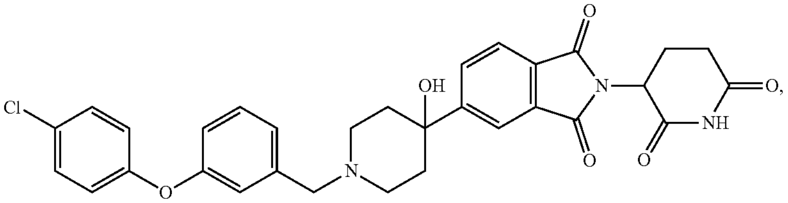

or a pharmaceutically acceptable salt thereof.

5. The compound of claim 1, which is (4)

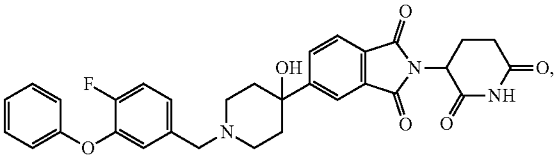

or a pharmaceutically acceptable salt thereof.

6. The compound of claim 1, which is (5)

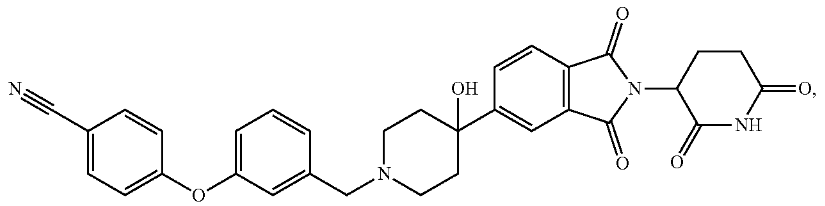

or a pharmaceutically acceptable salt thereof.

7. The compound of claim 1, which is (6)

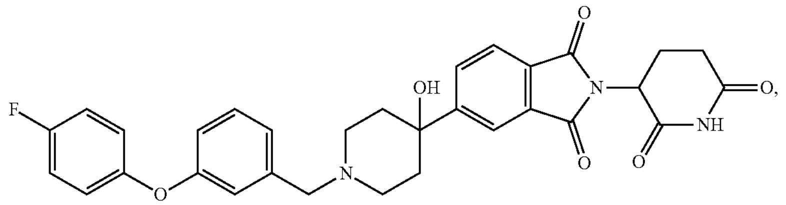

or a pharmaceutically acceptable salt thereof.

8. The compound of claim 1, which is (7)

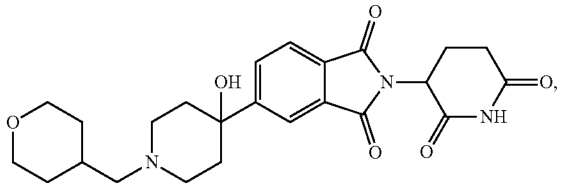

or a pharmaceutically acceptable salt thereof.

9. The compound of claim 1, which is (8)

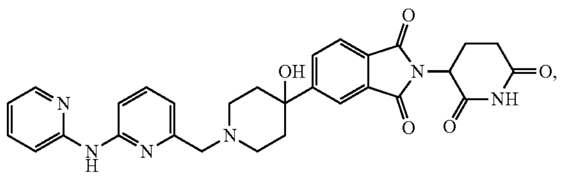

or a pharmaceutically acceptable salt thereof.

10. The compound of claim 1, which is (9)

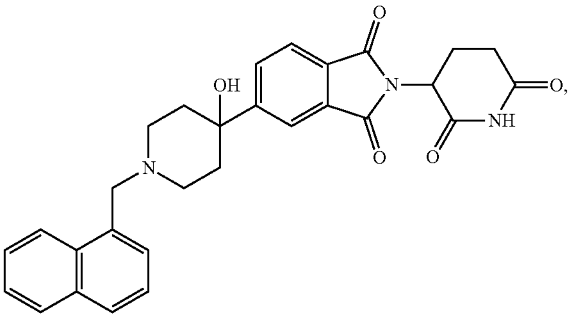

or a pharmaceutically acceptable salt thereof.

11. The compound of claim 1, which is (10)

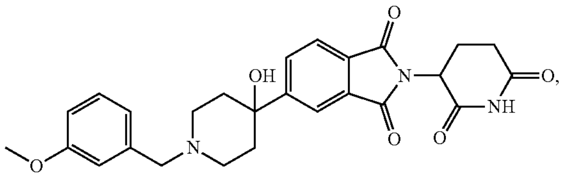

or a pharmaceutically acceptable salt thereof.

12. The compound of claim 1, which is (11)

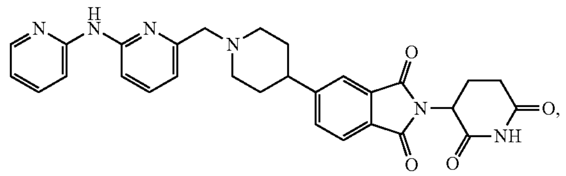

or a pharmaceutically acceptable salt thereof.

13. The compound of claim 1, which is (12)

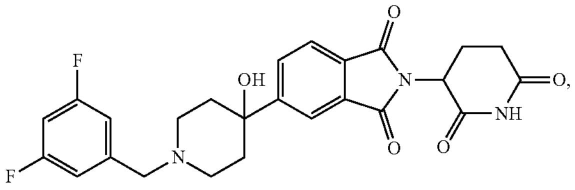

or a pharmaceutically acceptable salt thereof.

14. The compound of claim 1, which is (13)

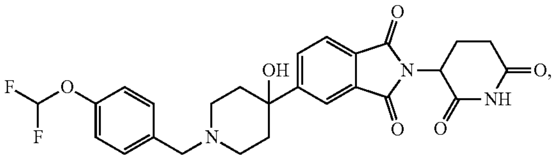

(14)

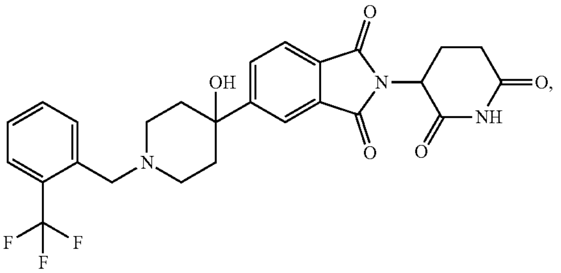

or a pharmaceutically acceptable salt thereof.

15. The compound of claim 1, which is (15)

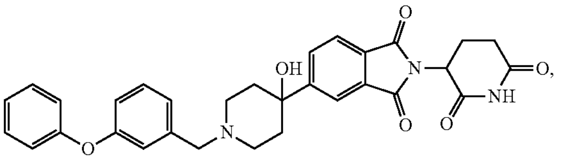

-continued (16)

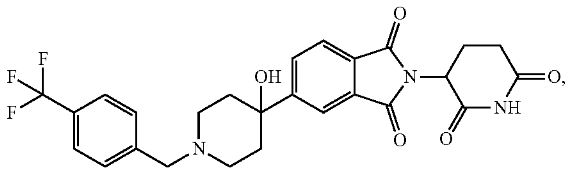

or a pharmaceutically acceptable salt thereof.

16. The compound of claim 1, which is (17)

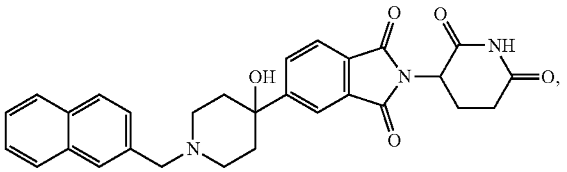

(18)

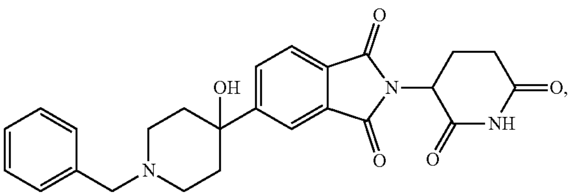

or a pharmaceutically acceptable salt thereof.

17. The compound of claim 1, which is (19)

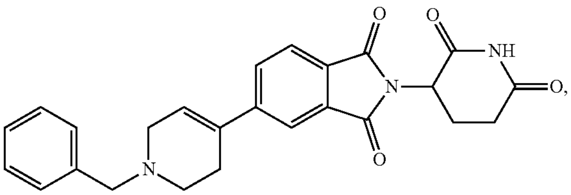

(20)

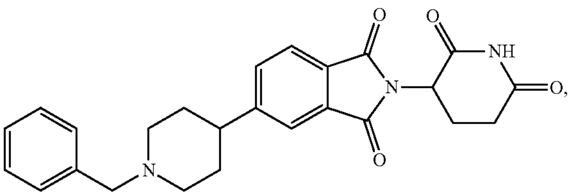

or a pharmaceutically acceptable salt thereof.

18. The compound of claim 1, which is in the form of a pharmaceutically acceptable salt.

19. A pharmaceutical composition, comprising a therapeutically effective amount of the compound or a pharmaceutically acceptable salt or stereoisomer thereof of claim 1, and a pharmaceutically acceptable carrier.

20. A method of treating a disease or disorder that is characterized or mediated by IKZF2 (Helios), comprising administering to a subject in need thereof a therapeutically effective amount of the compound or pharmaceutically acceptable salt or stereoisomer of claim 1.

* * * * *